US006608041B2

(12) United States Patent
Hammerly

(10) Patent No.: US 6,608,041 B2
(45) Date of Patent: Aug. 19, 2003

(54) ANALGESICS COMBINED WITH NATURALLY-OCCURRING CHONDROPROTECTIVE AGENTS

(76) Inventor: Milton Hammerly, 17602 Anton Ct., Parker, CO (US) 80134

( * ) Notice: Subject to any disclaimer, the term of this patent is extended or adjusted under 35 U.S.C. 154(b) by 92 days.

(21) Appl. No.: 09/784,384

(22) Filed: Feb. 15, 2001

(65) Prior Publication Data

US 2001/0046971 A1 Nov. 29, 2001

Related U.S. Application Data
(60) Provisional application No. 60/183,704, filed on Feb. 18, 2000.

(51) Int. Cl.$^7$ ........................ A01N 43/04; A61K 31/715
(52) U.S. Cl. ........................... 514/54; 514/62; 514/649
(58) Field of Search ............................. 514/54, 62, 649

(56) References Cited

U.S. PATENT DOCUMENTS

| | | | |
|---|---|---|---|
| 3,683,076 A | 8/1972 | Rovati | 424/180 |
| 3,697,652 A | 10/1972 | Rovati et al. | 424/180 |
| 4,647,453 A | 3/1987 | Meisner | 424/54 |
| 4,772,591 A | 9/1988 | Meisner | 514/62 |
| 4,801,619 A | 1/1989 | Lindblad | 514/825 |
| 5,364,845 A | 11/1994 | Henderson | 514/54 |

OTHER PUBLICATIONS

"Effects of Indomethacin on Joint Damage in Rat and Rabbit" Zhongguo Yao Li Xue Bao 1998 Jan;19(1):70–3 (ISSN:0253–9756) Wang B; Yao YY; Chen MZ Institute of Clinical Pharmacology, Anhui Medical University, Hefei, China.

"Effects of meloxicam compared to acetylsalicylic acid in human articular chondrocytes" Pharmacology 1997 Jan;54(1):49–56 (ISSN: 0031–7012) Bassleer C; Magotteaux J; Geenen V; Malaise M Department of Rheumatology, CHU, Liege 1, Belgium.

"Profile and mechanisms of gastrointestinal and other side effects of nonsteroidal anti–inflammatory drugs (NSAIDs)." Am J Med 1999 Dec. 13;107(6A):27S–35S; discussion 35S–36S (ISSN: 0002–9343) Rainsford KD Division of Biomedical Sciences and the Biomedical Research Centre, Sheffield Hallam University, United Kingdom.

"The influence of tissue cross–talking on OA progression: role of nonsteroidal antiinflammatory drugs." Osteoarthritis Cartilage 1999 Jul;7(4):374–6 (ISSN:1063–4584) Pelletier JP Director, Osteoarthritis Research Unit, Centre Hospitalier de l'Universite de Montreal(CHUM), Hopital Notre–Dame, 1560, rue Sherbrookest, Montreal, Quebec, H2L 4M1, Canada.

"Effects of some nonsteroidal anti–inflammatory drugs on articular cartilage of rats in an experimental model of osteoarthritis." Res Exp Med (Berl) 2001 Mar;200(3):215–26 (ISSN: 0300–9130) Gencosmanoglu BE; Eryavuz M; Dervisoglu S Istanbul Physical Medicine and Rehabilitation Center, Turkey.

"Effects of oral administration of phenylbutazone to horses on in vitro articular cartilage metabolism." Am J Vet Res 2001 Dec;62(12):1916–21 (ISSN: 0002–9645) Beluche LA; Bertone AL; Anderson DE; Rohde C Department of Veterinary Clinical Sciences, The Ohio State University, Columbus 43210, USA.

"Effects of meloxicam, compared with other NSAIDs, on cartilage proteoglycan metabolism, synovial prostaglandin E2, and production of interleukins 1,6 and 8, in human and porcine explants in organ culture" J Pharm Pharmacol 1997 Oct;49(10):991–8 (ISSN: 0022–3573) Rainsford KD; Ying C; Smith FC Division of Biomedical Sciences, School of Science and Mathematics, Sheffield Hallam University, UK.

"The role of glucosamine sulfate and chondroitin sulfates in the treatment of degenerative joint disease." Altern Med Rev 1998 Feb;3(1):27–39 (ISSN: 1089–5159) Kelly GS.

"Effects of antiinflammatory drugs on the progression of osteoarthritis of the knee." LINK Study Group. Longitudinal Investigation of Nonsteroidal Antiinflammatory Drugs in Knee Osteoarthritis. J Rheumatol 1995 Oct;22(10):1941–6(ISSN: 0315–162X) Huskisson EC; Berry H; Gishen P; Jubb RW; Whitehead J Department of Rheumatology, St. Bartholomew's Hospital, London, UK.

"Effects of the NSAIDs meloxicam and indomethacin on cartilage proteoglycan synthesis and joint responses to calcium pyrophosphate crystals in dogs." Vet Res Commun 1999 Mar;23(2):101–13 (ISSN: 0165–7380) Rainsford KD; Skerry TM; Chindemi P; Delaney K Division of Biomedical Sciences, School of Science and Mathematics, Sheffield Hallam University, Sheffield, UK.

*Primary Examiner*—Zohreh Fay
(74) *Attorney, Agent, or Firm*—Christopher J. Whewell

(57) ABSTRACT

Provided herein are medicinal compositions of matter that comprise a chondroprotective component and an analgesic component, wherein the chondroprotective component is naturally occurring in a preferred form of the invention, and the analgesic component is acetaminophen or its derivatives or analogs. The invention also provides procedures for administering the compositions to a patient who is afflicted with osteoarthritis.

20 Claims, No Drawings

ANALGESICS COMBINED WITH NATURALLY-OCCURRING CHONDROPROTECTIVE AGENTS

This application claims the benefit of U.S. Provisional Application No. 60/183,704 filed Feb. 18, 2000, the entire contents of which are herein incorporated by reference.

TECHNICAL FIELD

This invention relates to medicinal compositions of matter comprising an analgesic in combination with a naturally-occurring chondro-protective agent. The compositions according to the invention are suitable for oral administration. Alternatively, the combinations of the invention may be administered by any conventional means of drug administration.

BACKGROUND

Osteoarthritis ("OA") is the most common form of joint disease in the United States. It represents a major concern for health care providers because of its marked impact on the quality of life of those afflicted by it.

In healthy conditions, articular cartilage forms a smooth surface between articulating bone ends to reduce the friction caused by movement. This friction is further reduced by the synovial fluid. Articular cartilage consists of chondrocytes and two major macro-molecules; i.e., collagen and proteoglycans, which are synthesized by and deposited around the chondrocytes. The chondrocytes also synthesize the synovial fluid which bathes the articular cartilage.

The structural integrity of the articular cartilage is the foundation of optimal functioning of the skeletal joints in the hip, shoulders, elbows, hocks and stifles. Impaired function of skeletal joints will dramatically reduce mobility such as rising from sitting position or climbing and descending stairs. To maintain the structural integrity and the proper functioning of the articular cartilage, the chondrocytes constantly synthesize collagen and proteoglycans, the major components of the articular cartilage, as well as the friction-reducing synovial fluid. This constant synthesis of the macromolecules and synovial fluid provides the articular cartilage with the repairing mechanism for most of the wearing caused by friction between the bone ends. However, it also leads to the constant demand for the supply of precursors, or building blocks, for the macromolecules and synovial fluid. Lack of this precursors will lead to defects in the structure and function of the skeletal joints. This deficiency occurs often when activity levels are very high, or cartilage tissue has been traumatized.

An adequate supply of metabolic precursors or building blocks is thus paramount to replacement and repair of the constituents of skeletal joints, connective tissue and synovial fluid. Proteoglycans (or mucopolysaccharides) form the ground substance of cartilage, bone and joint fluid. Proteoglycans are comprised of proteins linked to glycosaminoglycans (GAGs). The building block GAG subunit of the proteoglycan in cartilage and bone is chondroitin sulfate. Chondroitin sulfate A is present in cornea and cartilage. Chondroitin sulfate B (G-heparin) is found in tendon, aorta, skin and heart valves. Chondroitin C is found in cartilage, tendon and umbilical cord and similar tissues. The building block GAG subunit of the proteoglycan in joint fluid is hyaluronic acid. Intercellular solutions of hyaluronic acid are viscous and thus assist in lubrication of the joints of body skeleton. Hyaluronic acid is synthesized from the metabolic precursor, glucosamine. The availability of glucosamine in cartilage tissue can be rate-limiting to the enzymatic step leading to the production of proteoglycans. Exogenous glucosamine serves to drive the biosynthetic pathway forward past the rate-limiting blockage point. Glucosamine serves as a substrate for a kinase enzyme which yields glucosamine-6-phosphate, the rate-limiting precursor in proteoglycan synthesis.

One class of materials that are commonly prescribed for the treatment of the symptoms of OA are the non-steroidal, anti-inflammatory drugs ("NSAIDS"). Many such compounds are known to those skilled in the art, including without limitation: Naproxen Sodium, Oxaprozin, Diclofenac, Etodolac/Lodine, Feldene, and Naprelan. While NSAIDS can provide symptomatic relief for those afflicted with OA, they are typically known to facilitate or accelerate the progression of OA by unfavorably altering the balance of destruction and repair in joints that are affected with OA. Further, NSAIDS have a known risk of liver toxicity, kidney toxicity, gastritis, ulcers, and gastrointestinal ("GI") bleeding. GI bleeding is believed to be the single largest contributing cause of the 100,000 deaths in the United States each year attributable to medication side effects (J.A.M.A. 4-98).

There is a class of compounds which may be generically referred to as naturally-occurring chondro-protective agents ("NOCPA's"). A wide range of NOCPA's are known to those skilled in the art, and include, without limitation, such compounds as glucosamine sulfate, chondroitin sulfate, N-acetyl glucosamine, hyaluronic acid and its derivatives such as hyaluronan, and the glycosaminoglycans. Numerous disclosures describe therapy of damaged tissues by introduction of such precursors in the metabolic pathway leading to biosynthesis of the macromolecules of connective tissues. For example, in U.S. Pat. No. 3,697,652 (Rovati et al.), N-acetylglucosamine is used to treat degenerative afflictions of the joints. In U.S. Pat. No. 3,683,076 (Rovati et al.), glucosamine salts are described as pharmaceutically useful for treatment of osteoarthritis and rheumatoid arthritis. U.S. Pat. No. 4,647,453 (Meisner) and U.S. Pat. No. 4,772,591 (Meisner) disclose the use of glucosamine salts for treatment of degenerative inflammatory disease and as a means of accelerating wound healing. In U.S. Pat. No. 4,801,619 (Lindblad), a hyaluronic acid preparation is claimed to be effective for treatment of steroid arthropathy and progressive cartilage degeneration caused by proteoglycan degradation. A combination of glucosamine, chondroitin and manganese is claimed in U.S. Pat. No. 5,364,845 (Henderson) as a means of protecting and repair of connective tissue. While these materials are capable of providing relief of symptoms of OA after about 4 to 6 weeks of administration, they offer no short term or immediate relief of OA symptoms. However, compounds within this broad class appear to have a chondroprotective effect which may favorably alter the progressive course of chronic OA. Generally, the NOCPA's are very safe and pose no substantial health risk associated with their use.

One common agent used in the rapid, short-term, symptomatic relief of the painful symptoms of osteoarthritis is acetaminophen, including its analogs and therapeutically effective derivatives, as such are known to those skilled in the art of medicinal chemistry. While having been the subject of much study in recent years owing to its widespread use, acetaminophen provides no long term relief to OA, nor does it have significant impact on the progression of OA.

None of these prior investigators, however, disclose a composition comprising an analgesic for short term relief from the symptoms of osteoarthritis in combination with a naturally-occurring chondroprotective agent that functions over the long term, and which thus work synergistically to simultaneously treat both the causality and the symptoms of OA.

SUMMARY OF THE INVENTION

The present invention is concerned with medicinal compositions of matter useful in the treatment of osteoarthritis. A composition according to the invention in general comprises an analgesic component and a chondro-protective agent. The analgesic component may comprise any material which is known to have analgesic properties, but preferably comprises a synthetic analgesic selected from the group consisting of: acetaminophen, an acetaminophen derivative, or an acetaminophen analog. In a preferred embodiment, the chondro-protective agent is naturally-occurring, and preferably comprises a glycosaminoglycan. However, other preferred chondro-protective agents may comprise a compound selected from the group consisting of: glucosamine sulfate, chondroitin sulfate, N-acetyl glucosamine, hyaluronic acid and hyaluronan.

According to a the invention, the analgesic component may be present in any amount between 0.05% and 99.5% by weight based upon the total weight of the composition, including every hundredth percentage therebetween. The chondro-protective component may be present in any amount between 0.05% and 99.5% by weight based upon the total weight of the composition, including every hundredth percentage therebetween.

Preparation of a composition according to the invention may be carried out by cocomminutation of the chondro-protective agent with the analgesic component. Alternatively, solutions of each component in water or other suitable solvent in which the selected components are mutually soluble may be provided and admixed with one another, the solvent being subsequently removed to provide an intimate mixture of the components.

The invention further comprises a process for treating osteoarthritis comprising the steps of first providing a composition according to the invention and subsequently introducing the composition into a human body that is afflicted with osteoarthritis. Although principally directed at treating humans, the inventive compositions may also be administered to mammals in general which suffer from osteoarthritis, including horses. It is preferred that the introduction of a composition according to the invention be carried out on at least a daily basis, for a time period sufficient for the benefits of a composition according to the invention to become manifest. It is preferred that the total mass of composition according to the invention to be introduced into a mammalian subject be in the range of between 0.500 grams and 10.00 grams, including every hundredth gram therebetween, per introduction, and each of the chondroprotective component and analgesic components be present in a therapeutically effective therapeutic amount. The introduction of a composition according to the invention may be undertaken orally, transdermally, buccally, intravenously, intramuscularly, parenterally, or sublingually using means known to those skilled in the art.

DETAILED DESCRIPTION

Analgesics including acetaminophen and its derivatives or analogs provide rapid relief from symptoms of OA which the NOCPA's cannot. The NOCPA's provide long-term benefits which acetaminophen or its derivatives and analogs cannot. Each of these types of materials complement each other by different, mutually-compatible mechanisms of action. A great advantage of the invention is that neither of these agents poses a risk of GI bleeding. The use of such novel combination to treat OA in the stead of NSAIDS when possible provides relief of symptoms, favorably alters disease progression, and is capable of preserving the lives of thousands of patients each year by eliminating the possibility of gastrointestinal bleeding.

In one preferred form, the present invention is directed at a therapeutically effective composition of matter which comprises acetaminophen (or one of its derivatives or analogs) and a naturally-occurring chondroprotective agent ("NOCPA") in combination with one another for simultaneous administration by the patient themselves, which is preferably oral administration of the composition in the form of a friable tablet, pill, or capsule. In embodiments, a combination according to the invention may be administered intravenously, intramuscularly, subcutaneously, parenterally, buccally, or sublingually.

The optimum dosage levels are dependent upon the NOCPA and acetaminophen used, the determination of such optimum levels being within the level of skill of one of ordinary skill in the art. In the case of glucosamine sulfate, a single daily dose of 1,500 milligrams per day per 150 pounds of body weight is an effective amount for total relief of symptoms or osteoarthritis after being administered 4 to 6 weeks. In the case of chondroitin sulfate, a dose of 1,200 milligrams per day per 150 pounds of body weight is an effective amount for relief of symptoms after being administered 4 to 6 weeks. The amount of acetaminophen needed for symptomatic relief preferably varies from 1,000 to 2,000 milligrams two to four times daily, depending upon the patient's individual needs.

EXAMPLE 1

400 grams of acetaminophen and 150 grams of chondroitin sulfate are placed into a mechanical mixer and cocomminutated until a homogeneous mixture is obtained. The composition according to Example 1 is suitable to be administered to a mammalian subject for the treatment of osteoarthritis by ingestion of 5.5 grams of such mixture on a daily basis.

EXAMPLE 2

400 grams of acetaminophen and 150 grams of glucosamine sulfate are placed into a mechanical mixer and cocomminutated until a homogeneous mixture is obtained.

EXAMPLE 3

400 grams of acetaminophen and 150 grams of N-acetyl glucosamine are placed into a mechanical mixer and cocomminutated until a homogeneous mixture is obtained.

EXAMPLE 4

400 grams of acetaminophen and 150 grams of hyaluronic acid are placed into a mechanical mixer and cocomminutated until a homogeneous mixture is obtained.

EXAMPLE 5

400 grams of acetaminophen and 150 grams of hyaluronan are placed into a mechanical mixer and cocomminutated until a homogeneous mixture is obtained.

EXAMPLE 6

4.00 grams of codeine and 150.00 grams of chondroitin sulfate are placed into a mechanical mixer and cocomminutated until 154 grams of a homogeneous mixture is obtained.

The composition according to Example 1 is suitable to be administered to a mammalian subject for the treatment of osteoarthritis by ingestion of 1.5 grams of such mixture on a daily basis.

EXAMPLE 7

4.00 grams of morphine and 150 grams of glucosamine sulfate are placed into a mechanical mixer and cocomminutated until a homogeneous mixture is obtained.

EXAMPLE 8

1.00 grams of demerol and 150 grams of N-acetyl glucosamine are placed into a mechanical mixer and cocomminutated until a homogeneous mixture is obtained.

EXAMPLE 9

1.00 grams of Percodan and 150 grams of hyaluronic acid are placed into a mechanical mixer and cocomminutated until a homogeneous mixture is obtained.

EXAMPLE 10

400 grams of aspirin and 150 grams of hyaluronan are placed into a mechanical mixer and cocomminutated until a homogeneous mixture is obtained.

EXAMPLE 11

4.00 grams of dyhydrocodeinone and 150.00 grams of chondroitin sulfate are placed into a mechanical mixer and cocomminutated until 154 grams of a homogeneous mixture is obtained.

The composition according to Example 1 is suitable to be administered to a mammalian subject for the treatment of osteoarthritis by ingestion of 1.5 grams of such mixture on a daily basis.

EXAMPLE 12

4.00 grams of Dialudid and 150 grams of glucosamine sulfate are placed into a mechanical mixer and cocomminutated until a homogeneous mixture is obtained.

EXAMPLE 13

1.00 grams of Dicodid and 150 grams of N-acetyl glucosamine are placed into a mechanical mixer and cocomminutated until a homogeneous mixture is obtained.

EXAMPLE 14

0.10 grams of Fentanyl and 150 grams of hyaluronic acid are placed into a mechanical mixer and cocomminutated until a homogeneous mixture is obtained.

EXAMPLE 15

400 grams of aspirin and 150 grams of hyaluronic acid are placed into a mechanical mixer and cocomminutated until a homogeneous mixture is obtained.

EXAMPLE 16

400 grams of aspirin and 150 grams of N-acetyl glucosamine are placed into a mechanical mixer and cocomminutated until a homogeneous mixture is obtained.

EXAMPLE 17

400 grams of aspirin and 150 grams of glucosamine sulfate are placed into a mechanical mixer and cocomminutated until a homogeneous mixture is obtained.

EXAMPLE 18

400 grams of aspirin and 150 grams of chondroitin sulfate are placed into a mechanical mixer and cocomminutated until a homogeneous mixture is obtained.

In addition, compositions according to the invention may be ingested infrequently or irregularly on an as-needed basis, in the same fashion as many individuals find it helpful to ingest an aspirin tablet on occasion without following a formal regiment.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

I claim:

1. A medicinal composition useful in the treatment of osteoarthritis comprising:
   a) an analgesic component; and
   b) a chondro-protective agent component.

2. A composition as set forth in claim 1 wherein said analgesic component comprises a compound selected from the group consisting of:
   acetaminophen, an acetaminophen derivative, or an acetaminophen analog.

3. A composition as set forth in claim 1 wherein said chondro-protective agent is naturally-occurring.

4. A composition as set forth in claim 1 wherein said chondro-protective agent comprises a glycosaminoglycan.

5. A composition as set forth in claim 1 wherein said chondro-protective agent comprises
   at least one compound selected from the group consisting of: glucosamine sulfate, chondroitin sulfate, N-acetyl glucosamine, hyaluronic acid and hyaluronan.

6. A composition according to claim 1 wherein said analgesic component is present in any amount between 0.05% and 99.5% by weight based upon the total weight of the composition, including every hundredth percentage therebetween.

7. A composition according to claim 1 wherein said chondro-protective component is present in any amount between 0.05% and 99.5% by weight based upon the total weight of the composition, including every hundredth percentage therebetween.

8. A composition according to claims 1 wherein said composition is prepared by cocomminutation of said chondro-protective agent with said analgesic component.

9. A composition according to claim 1 wherein the analgesic component is a compound selected from the group consisting of:
   acetaminophen, an acetaminophen derivative, or an acetaminophen analog, said analgesic component being present in any amount between 0.05% and 99.5% by weight based upon the total weight of the composition, including every hundredth percentage therebetween, and wherein said chondro-protective agent component is selected from the group consisting of:
   glucosamine sulfate, chondroitin sulfate, N-acetyl glucosamine, hyaluronic acid and hyaluronan, and wherein said chondro-protective component is present in any amount between 0.05% and 99.5% by weight based upon the total weight of the composition, including every hundredth percentage therebetween.

10. A composition according to claim 1 wherein the analgesic component is acetaminophen and is present in any amount between 0.05% and 99.5% by weight based upon the total weight of the composition, including every hundredth percentage therebetween, and wherein said chondro-protective agent component is selected from the group consisting of:

glucosamine sulfate, chondroitin sulfate, N-acetyl glucosamine, hyaluronic acid and hyaluronan, and wherein said chondro-protective component is present in any amount between 0.05% and 99.5% by weight based upon the total weight of the composition, including every hundredth percentage therebetween.

11. A process for treating osteoarthritis comprising the steps of:

a) providing a composition according to claim 1; and b) introducing said composition into a human body that is afflicted with osteoarthritis.

12. A process according to claim 11 further comprising the step of:

c) repeating step b) at least one times per day for a period of at least 3 weeks.

13. A process for treating osteoarthritis comprising the steps of:

a) providing a composition according to claim 9; and b) introducing said composition into a human body that is afflicted with osteoarthritis.

14. A process according to claim 13 further comprising the step of c) repeating step b) at least one times per day for a period of at least 3 weeks.

15. A process for treating osteoarthritis comprising the steps of:

a) providing a composition according to claim 10; and b) introducing said composition into a human body that is afflicted with osteoarthritis.

16. A process according to claim 15 further comprising the step of:

c) repeating step b) at least one times per day for a period of at least 3 weeks.

17. The process according to claim 11 wherein said composition contains a therapeutically effective therapeutic amount of chondro-protective agent component.

18. The process according to claim 11 wherein said composition contains a therapeutically effective therapeutic amount of analgesic component.

19. A process according to claim 11 wherein said introducing is undertaken orally, buccally, intravenously, intramuscularly, parenterally, or sublingually.

20. A process for treating osteoarthritis comprising the step of simultaneously introducing a therapeutically effective amount of an analgesic and a therapeutically effective amount of a naturally-occurring chondroprotective agent to a mammalian subject.

* * * * *